United States Patent [19]

Bannon

[11] 4,436,533
[45] Mar. 13, 1984

[54] ADSORPTION PROCESS

[75] Inventor: Robert P. Bannon, Houston, Tex.

[73] Assignee: Shell Oil Company, Houston, Tex.

[21] Appl. No.: 446,299

[22] Filed: Dec. 2, 1982

[51] Int. Cl.³ .......................................... B01D 53/04
[52] U.S. Cl. ............................................ 55/26; 55/62; 55/75; 585/826
[58] Field of Search ............... 55/25, 26, 58, 62, 75; 585/820-822, 826-829

[56] References Cited

U.S. PATENT DOCUMENTS

| | | | |
|---|---|---|---|
| 2,985,589 | 5/1961 | Broughton et al. | 585/826 X |
| 3,176,444 | 4/1965 | Kiyonaga | 55/26 |
| 3,430,418 | 3/1969 | Wagner | 55/62 X |
| 3,451,924 | 6/1969 | Helfferich et al. | 585/826 X |
| 3,636,679 | 1/1972 | Batta | 55/62 X |
| 3,738,087 | 6/1973 | McCombs | 55/62 X |
| 4,077,779 | 3/1978 | Sircar et al. | 55/25 |
| 4,176,053 | 11/1979 | Holcombe | 585/822 X |
| 4,238,321 | 12/1980 | Florack | 585/826 X |
| 4,350,501 | 9/1982 | Bannon | 55/26 |
| 4,358,367 | 11/1982 | Bannon | 585/826 X |
| 4,359,380 | 11/1982 | Bannon | 585/826 X |
| 4,371,380 | 2/1983 | Benkmann | 55/26 |
| 4,402,712 | 9/1983 | Benkmann | 55/26 |

Primary Examiner—Robert H. Spitzer

[57] ABSTRACT

A continuous, cyclic, vapor-phase adsorption process for the separation of normal paraffins from a hydrocarbon feed mixture, providing improved efficiency of separation and continuity in product flows. For purposes of this process, a continuous flow of the feed mixture and a continuous flow of an eluent are passed in repetitions of a particular sequence of nine process steps to at least three molecular sieve adsorbent beds.

8 Claims, 15 Drawing Figures

(PRIOR ART)

4,436,533

ADSORPTION PROCESS

BACKGROUND OF THE INVENTION

This invention relates to an improved continuous adsorption process for the resolution of hydrocarbon mixtures into products of like molecular structure. More particularly, this process relates to the application of multiple molecular sieve adsorbent beds to the separation of normal paraffins from a vapor-phase hydrocarbon mixture containing the same.

It is recognized that resolution of the components of certain fluid solutions can be achieved through exploitation of the adsorptive properties of materials commonly known as molecular sieves. Such materials, principally the natural and synthetic aluminosilicates, have a porous crystalline structure with intracrystal cavities that are accessible via pores of relatively uniform diameter. Adsorption through the pores is selective—only molecules with an effective diameter smaller than the characteristic pore diameter of a particular molecular sieve can be adsorbed thereby. Thus, a basis is provided for separation of molecules according to size. Molecular sieves are particularly useful for accomplishing the separations of mixtures of hydrocarbons of differing molecular structures, for instance the separation of normal paraffins from mixtures also comprising branched and/or cyclic hydrocarbons, which separations are not generally feasible through more common techniques such as fractional distillation or solvent extraction.

In the application of a molecular sieve to such separations, a mixed feedstock is passed over a contained bed of the sieve material to accomplish adsorption thereon of selected molecules, termed the adsorbate fraction of the feedstock. Effluent from the bed comprises the remaining fraction of the feedstock, herein termed the raffinate. Adsorption is, of course, but one phase of the overall separation process, since the adsorbate must eventually be desorbed from the sieve. One common method for accomplishing such desorption involves discontinuing the flow of feedstock and passing a stream of an eluent over the bed. The eluent is generally a compound which is itself adsorbed through the sieve pores. For instance, when the adsorbate is a normal paraffin of a given carbon number, a preferred eluent is a normal paraffin of a different carbon number. In this case both the adsorption and desorption phases of the overall separations process involve interchange of eluent and adsorbate molecules on the sieve bed—adsorbate molecules are displaced from the sieve pores by eluent molecules during the desorption step and eluent is displaced by adsorbate during a subsequent adsorption step. A mixture of raffinate and eluent molecules is withdrawn as effluent from the bed during adsorption service by the bed, and a mixture of adsorbate and eluent is withdrawn during desorption. Such effluent mixtures, respectively termed the process raffinate and adsorbate products, are generally then subjected to further processing for the recovery of eluent for recycle to the adsorption beds.

With respect to the use of a given sieve bed for separations purposes, the performance of distinct adsorption and desorption steps does not permit a continuous process as is often desired for efficient commercial operations. It is recognized, however, that certain discontinuities associated with the use of a single bed can be eliminated and other processing advantages realized through the use of multiple sieve beds.

In the context of vapor-phase adsorption processes for the separation of normal paraffins from hydrocarbon mixtures, one such multi-bed process which has proven to be of particular advantage is that of U.S. Pat. No. 3,451,924. Through repeated switching of process flows to three adsorbent beds in a 6 step sequence, the process of this patent achieves continuity with respect to the flow of both hydrocarbon feed and eluent to the beds. Furthermore, through series flow of certain process streams through two adsorbent beds, the process provides for loading of each adsorbent bed to near full capacity without loss of the normal paraffins to the process raffinate product.

The prior art process of U.S. Pat. No. 3,451,924 can be more particularly described through reference to attached FIG. 1, which in six parts, labeled (a) through (f), illustrates schematically each of the six process steps. Referring to FIG. 1(a), depicted therein is a step of the process in which a continuous flow of a vapor-phase normal paraffin-containing mixed hydrocarbon feed stream designated 10 is passed to a first sieve bed designated A which functions as a primary adsorption bed to adsorb said feed normal paraffins. Effluent, stream 11, is withdrawn from bed A and passed to another bed labeled B which serves as a secondary adsorption bed, capturing normal paraffins which escape adsorption in, or "breakthrough", sieve bed A. A process raffinate product, stream 20, composed primarily of non-normal paraffin hydrocarbons from the feed and of eluent, is withdrawn from bed B. This raffinate mixture is typically separated into an eluent fraction and a non-normal paraffin hydrocarbon fraction by downstream processing facilities not a part of the adsorption process and not here shown. The separated eluent fraction is usually recycled. Also during the process step depicted in FIG. 1(a), a continuous flow of eluent 30 is passed to a previously loaded bed C for desorption of normal paraffins therein. A process adsorbate product 40 is withdrawn from bed C. This adsorbate product is then typically separated into a feed normal paraffin fraction and an eluent fraction by downstream processing facilities not shown, and the eluent recycled to the adsorption process.

The prior art process step depicted in FIG. 1(a) is continued until bed A is loaded to substantially full capacity with adsorbate and desorption of bed C is essentially complete, at which time process flows are switched to the step of FIG. 1(b). Now, referring to this Figure, the continuous flow of hydrocarbon feed, again designated 10, is passed directly to sieve bed B which serves as a sole adsorption bed for this process step. The continuous eluent flow 30 is passed to bed A to purge non-adsorbed feed hydrocarbons from the void spaces therein before the bed is subjected to desorption. The purge effluent stream 31 from purge bed A contains quantities of unadsorbed normal paraffins purged from the void spaces, as well as quantities of normal paraffins unavoidably desorbed from the seive bed by the flow of eluent. For this reason, it is passed to freshly desorbed bed C which serves as a purge guard bed wherein these normal paraffins can be recaptured. Effluent from bed B and effluent from bed C, both composed substantially of feed non-normal paraffin hydrocarbons and eluent, may be combined as shown into a single raffinate product 20. Alternatively, the two effluent streams may be maintained as separate raffinate products for downstream use or processing. There is no process adsorbate product stream during the process step of FIG. 1(b).

Once bed A has been effectively purged of non-normal paraffin hydrocarbons, process flows are switched to the step illustrated in FIG. 1(c). This step is in principle very similar to that of FIG. 1(a), as is indicated by process stream designations common to the two figures. Here, however, bed A is the desorption bed, bed B is the primary adsorption bed, and bed C is the secondary adsorption bed. The process is in turn switched to the steps of FIGS. 1(d), 1(e), and 1(f). Upon completion of the step of FIG. 1(f), the process is switched to that of FIG. 1(a). The six step process sequence is continuously repeated in this manner as many times as is desired. The service of each bed in each of the six process steps is summarized in Table 1:

TABLE 1

|  | bed A | bed B | bed C |
|---|---|---|---|
| The step of: |  |  |  |
| FIG. 1(a) | primary adsorption | secondary adsorption | desorption |
| FIG. 1(b) | purge | sole adsorption | purge guard |
| FIG. 1(c) | desorption | primary adsorption | secondary adsorption |
| FIG. 1(d) | purge guard | purge | sole adsorption |
| FIG. 1(e) | secondary adsorption | desorption | primary adsorption |
| FIG. 1(f) | sole adsorption | purge guard | purge |

In view of the continuous cyclic nature of this process, it has been termed the "Merry-Go-Round" process.

Despite the commercial success which the process of U.S. Pat. No. 3,451,924 has enjoyed, there are a number of disadvantages associated with its operation and performance. For instance, it is observed through reference to FIG. 1 that the purge guard service of each sieve bed is followed immediately by its secondary adsorption service. In both services, the effluent flow from the particular bed is taken from the process as raffinate product. Each switch from purge guard service to secondary adsorption service results in drastic changes in the composition of the process raffinate product stream. These changes occur because at the time the switch takes place the vapor in the bed consists essentially of eluent, introduced during the purge guard operation. Before the switch, the effluent from the particular bed, and the total process raffinate product, contain substantial quantities of both eluent and non-normal paraffin hydrocarbons. For a short time after the switch, the effluent from the bed, and the process raffinate product consist almost entirely of eluent. The effluent from the bed, and the process raffinate product, then quickly return to a mixture containing a substantial amount of non-normal paraffin hydrocarbon. Because of such discontinuities in its composition, which are periodically repeated in the process cycle, downstream processing of the vapor-phase raffinate product stream has proved most difficult. For example, it has been impossible to implement efficient heat conservation measures or fully stable downstream processes for eluent recovery.

Furthermore, the sequence under which beds in purge guard service (process steps of FIGS. 1(b), 1(d), and 1(f)) are next switched to secondary adsorption service (process steps of FIGS. 1(c), 1(e), and 1(a), respectively) has adverse effects upon the normal paraffin adsorption capacity of the beds. In its purge guard service, a significant amount, e.g., 20% of working capacity, of normal paraffins are adsorbed over a somewhat broad adsorption front in the sieve bed. The adsorption front becomes broader still when the bed is next switched to secondary adsorption service. The flowrate of the process stream it then receives, and the relatively high eluent content of the bed (both eluent that is already contained in the bed as a result of the purge guard duty and eluent that has been displaced from the upstream primary adsorption bed) combine to push already adsorbed feed normal paraffins further downstream in the bed. As a consequence, when hydrocarbon feed is passed over the bed during its subsequent sole primary adsorption services, breakthrough of feed normal paraffins into the bed effluent is more severe and is encountered well before the bed is substantially loaded.

In addition to the Merry-Go-Round process, several other multi-bed adsorption processes are known to the art for continuous separation of vapor-phase hydrocarbon mixtures, including those described in U.S. Pat. No. 2,985,589, U.S. Pat. No. 4,176,053, and U.S. Pat. No. 4,238,321.

U.S. Pat. No. 4,358,367 issued Nov. 9, 1982, U.S. Pat. No. 4,359,380 issued Nov. 16, 1982, and U.S. Pat. No. 4,350,501 issued Sept. 21, 1982, all of common inventorship with the instant application, describe still other multi-bed, continuous adsorption processes.

SUMMARY OF THE INVENTION

The instant invention provides an improved multi-bed continuous cyclic vapor-phase process for the separation of normal paraffins from a hydrocarbon mixture containing normal paraffins and non-normal paraffin hydrocarbons, which substantially alleviates the aforementioned problems associated with the prior art. According to the invention, a continuous flow of a feed mixture and a continuous flow of an eluent are passed in repetitions of a particular sequence of nine process steps to at least three adsorbent beds to accomplish separation of the mixture into an adsorbate product fraction comprising normal paraffins and a raffinate product fraction comprising non-normal paraffin hydrocarbons. The process steps may be described as follows: step one, in which the feed mixture is passed through a first adsorbent bed, effluent is withdrawn from the first bed and passed through a second adsorbent bed, the eluent flow is passed through a third adsorbent bed, adsorbate product is withdrawn as an effluent from the third bed, and raffinate product is withdrawn as an effluent from the second bed;

step two, in which the feed mixture is passed through the second bed, the eluent flow is passed through the first bed, effluent from the first bed is withdrawn and is passed through the third bed, and raffinate product is withdrawn as effluent from the second bed and from the third bed;

step three, in which the feed mixture is passed through the second bed, the eluent flow is passed through the first bed, adsorbate product is withdrawn as effluent from the first bed, effluent from the second bed is withdrawn and is divided into a major fraction and a minor fraction,
said minor fraction is passed through the third bed, and
raffinate product is withdrawn as said major fraction of effluent from the second bed and as effluent from the third bed;

step four, in which
the feed mixture is passed through the second bed,
effluent is withdrawn from the second bed and passed through the third bed,
the eluent flow is passed through the first bed,
adsorbate product is withdrawn as an effluent from the first bed, and
raffinate product is withdrawn as an effluent from the third bed;

step five, in which
the feed mixture is passed through the third bed,
the eluent flow is passed through the second bed,
effluent from the second bed is withdrawn and is passed through the first bed, and
raffinate product is withdrawn as effluent from the first bed and from the third bed;

step six, in which
the feed mixture is passed through the third bed,
the eluent flow is passed through the second bed,
adsorbate product is withdrawn as effluent from the second bed,
effluent from the third bed is withdrawn and is divided into a major fraction and a minor fraction,
said minor fraction is passed through the first bed, and
raffinate product is withdrawn as said major fraction of effluent from the third bed and as effluent from the first bed;

step seven, in which
the feed mixture is passed through the third bed,
effluent is withdrawn from the third bed and passed through the first bed,
the eluent flow is passed through the second bed,
adsorbate product is withdrawn as an effluent from the second bed, and
raffinate product is withdrawn as an effluent from the first bed; and step eight, in which
the feed mixture is passed through the first bed, the eluent flow is passed through the third bed,
effluent from the third bed is withdrawn and is passed through the second bed, and
raffinate product is withdrawn as effluent from the first bed and from the second bed; and step nine, in which
the feed mixture is passed through the first bed,
the eluent flow is passed through the third bed,
adsorbate product is withdrawn as effluent from the third bed,
effluent from the first bed is withdrawn and is divided into a major fraction and a minor fraction,
said minor fraction is passed through the second bed, and
raffinate product is withdrawn as said major fraction of effluent from the first bed and as effluent from the second bed.

In practice, the separation process of the invention has the advantages which have characterized the conventional multi-bed molecular sieve adsorption process of U.S. Pat. No. 3,451,924. As with this known process, the invention can be carried out in only three adsorbent beds and with continuous flows of both feedstock and eluent. The invention likewise provides a secondary adsorption bed which prevents the breakthrough of normal paraffins into the raffinate product as the primary adsorption bed nears full capacity.

Additionally, practice of the process of the invention provides substantial advantages over the prior art. For instance, under the invention the magnitude of changes in the composition of the raffinate product throughout the repeated sequential switching between the various process steps is substantially reduced. This aspect of the invention makes possible a more stable operation of downstream processing equipment, including more efficient energy conservation.

The invention affords still further benefit over the process of U.S. Pat. No. 3,451,924 by eliminating much of the previously-described problem associated with the spreading of the adsorption front in the bed when it is switched from its purge guard to its secondary adsorption service. As a result, the invention may be practiced to realize a higher throughput of feedstock for a given quality of separation or, alternatively, a higher degree of separation at a given throughput.

Under the invention, this switching of services, from purge guard to secondary adsorption, is accomplished slowly—only a minor fraction of the sole adsorption bed effluent is passed (at first) to the particular bed. In effect, this minor fraction functions to slowly purge high concentrations of eluent before the bed is placed in its secondary adsorption service. The passing of this minor fraction through the bed is for this reason termed a pre-adsorption purge service, and is to be distinguished from the predesorption purge carried out both in this process as well as in the prior art to prevent contamination of adsorbate product with feed non-normal hydrocarbons.

DESCRIPTION OF THE PREFERRED EMBODIMENTS

The invention summarily described above can be more fully illustrated through reference to the attached FIG. 2. Schematically depicted therein is the operation of three molecular sieve beds, designated A, B, and C, through a sequence of nine process steps each of which is individually shown in the parts of FIG. 2 labeled FIG. 2(a) through FIG. 2(i).

Figure 1A:
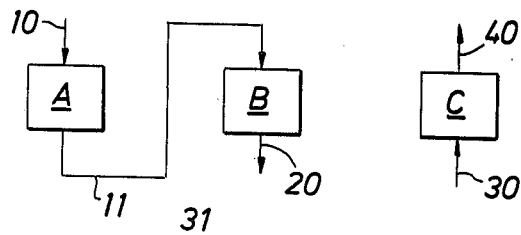
Figure 1B:
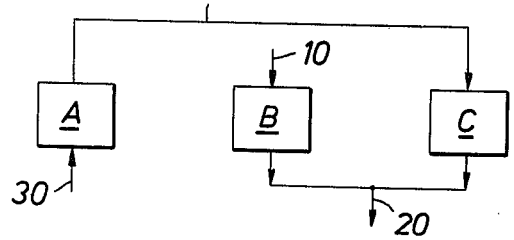
Figure 1C:
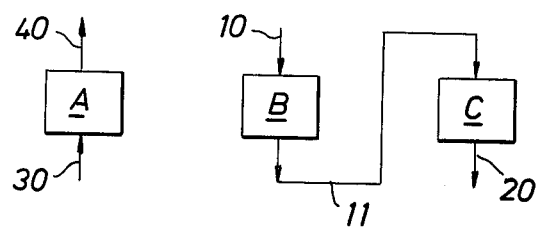
Figure 1D:
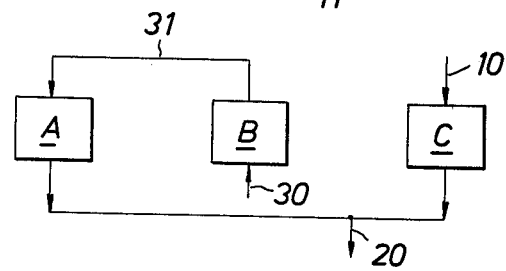
Figure 1E:
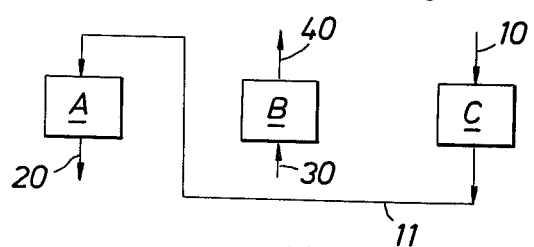
Figure 1F:
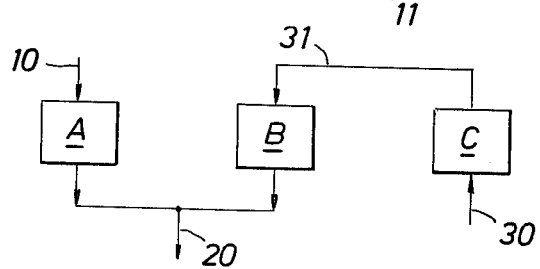
Figure 2A:
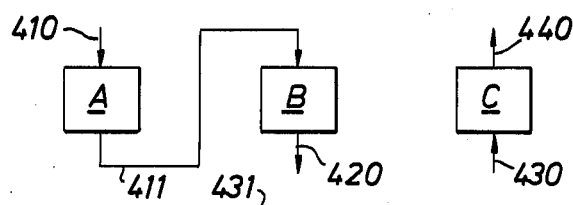

Looking first to FIG. 2(a), illustrated therein is step one of a cyclic process according to the invention, in which step a continuous flow of a vapor-phase normal paraffin-containing hydrocarbon feed stream designated 410 is passed to sieve bed A which functions as a primary adsorption bed to adsorb said normal paraffins. Effluent, stream 411, is withdrawn from bed A and passed to a second bed B which serves as a secondary adsorption bed, capturing feed normal paraffins which break through sieve bed A. A process raffinate product, stream 420, with a feed normal paraffin content substantially reduced from that of stream 410, is withdrawn from bed B. Also during the process step depicted in FIG. 2(a), a continuous flow of eluent vapor 430 is passed to bed C, which has been previously loaded with feed normal paraffins, for desorption thereof from the sieve. A process adsorbate product 440, containing essentially feed normal paraffins and eluent, is withdrawn from this desorption bed.

Figure 2B:
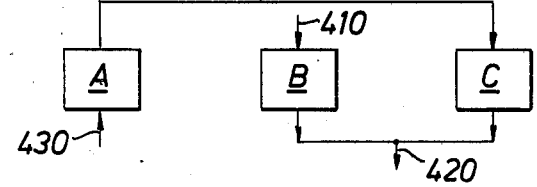
Figure 2C:
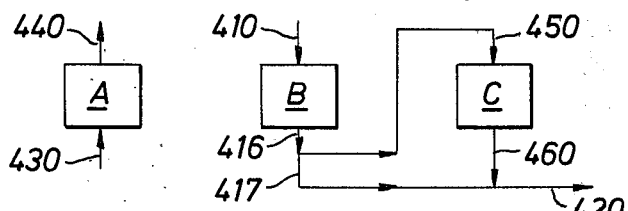
Figure 2D:
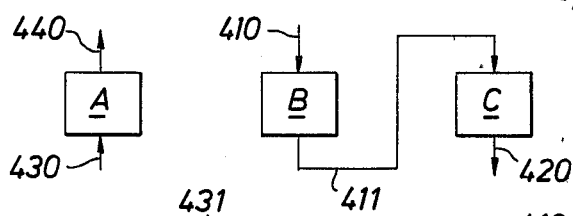

The process step depicted in FIG. 2(a) is continued until bed A is loaded to substantially full capacity with feed normal paraffins and desorption of bed C is essentially complete, at which time the process is switched to step two illustrated by FIG. 2(b). Referring to this Figure, the continuous flow of hydrocarbon feed 410 is passed directly to sieve bed B which serves as a sole adsorption bed for this process step, to adsorb feed normal paraffins. The continuous eluent flow 430 is passed to bed A for pre-desorption purge of non-adsorbed feed hydrocarbons from the void spaces therein. An effluent stream 431 is withdrawn from bed A and passed to bed C which serves as a purge guard bed, capturing normal paraffins in the pre-desorption purge effluent which would otherwise be lost. Effluent from bed B and effluent from bed C, both composed substantially of feed non-normal paraffin hydrocarbons and eluent, may be combined as shown into a single raffinate product 420. Alternatively, the two effluent streams may be maintained as separate raffinate products for downstream use or processing.

Step two is continued until the void spaces of bed A have been effectively purged of feed non-normal paraffin hydrocarbons. Process flows are then switched to step three shown in FIG. 2(c). During this step, the continuous flow of eluent 430 to bed A continues. Bed A is now in desorption service, however, and effluent 440 is taken as process adsorbate product. The continuous flow of feed 410 to sole adsorption bed B also continues. Effluent 416 is withdrawn from bed B and is divided into two streams: a minor fraction 450 and a major fraction 417. The minor fraction 450 (between about 5 and 50 percent of stream 416) is passed through bed C, which is operating in a preadsorption purge mode. The eluent content of the void spaces of bed C is thereby substantially reduced, as eluent-rich vapor is replaced by effluent vapor from bed B. While bed B effluent contains eluent displaced from the bed B sieve during adsorption service, the concentration of eluent in bed B effluent is substantially lower than that of the vapor contained in the void spaces of bed C as a result of its previous purge guard service. The major fraction 417 (between about 50 and 95 percent) of bed B effluent 416 is taken from the process as raffinate product. The effluent 460 from bed C is likewise taken from the process as raffinate, either alone or, as shown, in a combination with stream 417 as total raffinate 420.

Step three is continued until the eluent concentration in the void space vapor in bed C has been significantly reduced and bed B is approaching a loading beyond which significant breakthrough of normal paraffins would occur. Process flows are then switched to the practice of step four shown in FIG. 2(d). Desorption of bed A continues in this step, as eluent 430 is passed through the bed and effluent is withdrawn as adsorbate product 440. The flow of feed 410 to bed B continues. Bed B is now, however, in a primary adsorption service, and effluent 411 is passed through bed C, the secondary adsorption bed to capture feed normal paraffin which breaks through bed B. Raffinate product 420 is withdrawn as effluent from bed C.

Figure 2E:
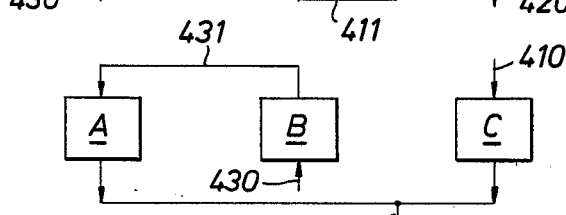

Once bed B has been substantially loaded with feed normal paraffins and desorption of bed A is essentially complete through operation of step four, the process is switched to step five, illustrated by FIG. 2(e). In this step, eluent 430 is passed through bed B, now undergoing pre-desorption purge. Effluent 431 from bed B is passed through purge guard bed A. Process feed is passed through sole adsorption bed C. Raffinate product is withdrawn from both bed A and bed C, and may suitably be combined into a single stream 420 as shown.

Figure 2F:
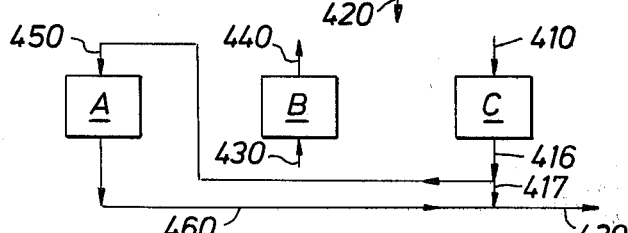
Figure 2G:
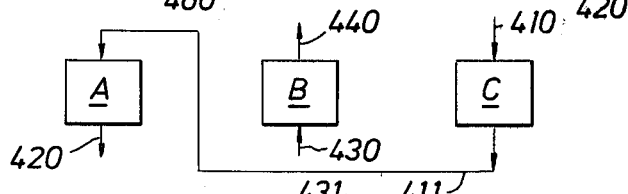

Upon completion of the pre-desorption purge of bed B in step five, the process is switched to step six, shown in FIG. 2(f). Bed B is now in desorption service. Eluent 430 is passed through bed B and adsorbate product taken as effluent 440. Process feed 410 is passed through bed C which is in a sole adsorption mode. Bed C effluent 416 is withdrawn and divided into a major fraction 417 (about 50 to 95 percent of the total) and a minor fraction 450 (about 5 to 50 percent of the total). The minor fraction is passed through bed A for pre-adsorption purge to reduce content of the eluent in the bed's void spaces. Effluent 460 from bed A and the major fraction 417 are withdrawn, either separately or together as raffinate product 420.

Step six continued until the content of eluent in the void spaces of bed A is substantially reduced and bed C is approaching a loading beyond which significant breakthrough of normal paraffins would occur. The process is then switched to step seven, illustrated in FIG. 2(g). For step seven, the flow of eluent 430 to bed B in desorption service continues, and adsorbate product 440 is withdrawn. Process feed flow 410 continues to bed C in primary adsorption service. The full flow of effluent 411 from bed C is passed through bed A in secondary adsorption service. Effluent 420 from bed A is withdrawn as raffinate product.

Figure 2H:
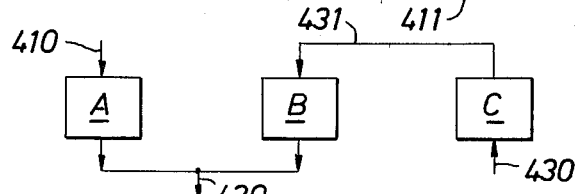

Once bed C has been substantially loaded with feed normal paraffins and desorption of bed B is essentially complete under practice of step seven, the process is switched to step eight, shown in FIG. 2(h). In this step, eluent is passed to bed C, now undergoing pre-desorption purge for removal of feed non-normal paraffins from the void spaces. Effluent 431 is withdrawn from bed C and passed through bed B in purge guard service for recovery of feed normal paraffins therein. Feed 410 is passed through bed A in sole adsorption service. Effluent from bed A and effluent from bed B are withdrawn, either alone or in combination as raffinate product 420.

Figure 2I:
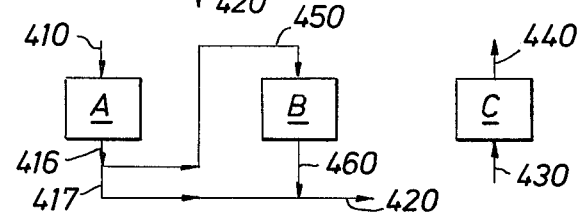

Step eight is continued until the void spaces of bed C are effectively purged of feed non-normal hydrocarbons, at which time the process is switched to step nine, illustrated in FIG. 2(i). Bed C is now in desorption service, with eluent 430 passed therethrough to desorb feed normal paraffins from the sieve. Adsorbate product 440 is withdrawn from bed C. Process feed 410 is passed to bed A in sole adsorption service, for adsorption by the sieve therein of feed normal paraffins. Effluent 416 from bed A is withdrawn and divided into a major fraction 417 (about 50 to 95 percent of the total) and a minor fraction 450 (about 5 to 50 percent of the total). The minor fraction is passed through bed B in pre-adsorption purge service, to reduce the eluent content of the void spaces of this bed. Effluent 460 from bed B, and the major fraction 417 of effluent from bed A are withdrawn, either separately or together as raffinate product 420.

Upon completion of step nine, i.e., when eluent content of the vapor in the void spaces of bed B has been significantly reduced and bed A has approached a loading beyond which significant breakthrough would occur, the process of invention has undergone one full cycle. Process flows are now switched to step one and the sequence of steps one through nine repeated in the manner described above as many times as is desired.

The functions of each of the three sieve beds in each of the nine process steps of the invention are recited in Table II.

TABLE II

| | bed A | bed B | bed C |
|---|---|---|---|
| Step one | primary adsorption | secondary adsorption | desorption |
| Step two | pre-desorption purge | sole adsorption | purge guard |
| Step three | desorption | sole adsorption | pre-adsorption purge |
| Step four | desorption | primary adsorption | secondary adsorption |
| Step five | purge guard | pre-desorption purge | sole adsorption |
| Step six | pre-adsorption purge | desorption | sole adsorption |
| Step seven | secondary adsorption | desorption | primary adsorption |
| Step eight | sole adsorption | purge guard | pre-desorption purge |
| Step nine | sole adsorption | pre-adsorption purge | desorption |

For the sake of clarity, FIG. 2, through which the invention is described above, omits a detailed showing of the full array of interconnecting flow conduits, valves, and optional instrumentation which are employed to switch the process flows through the invention's full cycle of nine steps. The description of the invention herein also omits detailed description of known procedures for the use of one or more beds in addition to the three required for practice of the invention to enable periodic regeneration of each bed. For instance, a fourth adsorbent bed can be provided so that process continuity is maintained during regeneration of one bed, in which case the nine step process description applies to the remaining three beds which are utilized at any given time. Such equipment and procedures and their operation are considered obvious to one skilled in the art and thus do not require elaborate description herein.

It is critical to the process of the invention that during steps three, six, and nine, as above-described, the effluent flow from the bed in sole adsorption service is divided into a major fraction which is taken directly as raffinate product and a minor fraction which is passed through the bed which had in the immediately preceding step served as a purge guard bed. The division of this flow is necessarily such that between about 5 and 50 percent of the eluent flow during these steps is provided as the minor fraction and the remaining approximately 50 to 95 percent is taken as the major fraction. The practical limits upon the division of this flow into such major and minor fractions are determined by consideration of the minimum volume of pre-adsorption purge flow which is necessary to fill the void space of the purge bed and of the maximum desirable fluctuation in raffinate composition during course of the pre-adsorption purge. Preferably, the process of the invention is operated such that the minor fraction is between about 7 and 40 volume percent of the total sole adsorption bed effluent flow in steps three, six, and nine. More preferably, the minor fraction during these steps is between about 10 and 30 volume percent of total adsorption effluent, the remaining 70 to 90 volume percent being taken directly as raffinate product. Most preferably, the minor fraction is between about 12 and 25 percent, and the major fraction is between about 75 and 88 percent of the adsorption bed effluent.

Pre-adsorption purge, according to steps three, six, and nine of the invention, was not practiced in related prior art adsorption processes. In either the process of the invention or that of the prior art the sole adsorption service of a bed continues only so long as the bed is able to prevent substantial breakthrough of normal paraffins into the raffinate product. During practice of the process of the invention, the adsorption front in the sole adsorption bed is sharper, working capacity of the sieve is increased, and breakthrough is delayed. This, in turn, provides opportunity for the operation of the pre-adsorption purge step of another bed following its purge guard duty. Since breakthrough is delayed, there is no need to put the other bed into secondary adsorption service immediately after completion of purge guard service.

For purposes of practice of the cycle of process steps of the invention described above, it is necessary that consideration be given to such matters as the type and amount of molecular sieve to be employed in the multiple adsorption beds, the operating temperatures and pressures of the beds and the several process vapor streams, the flowrates and compositions of feed and eluent, and the periodic regeneration of each sieve bed. Generally, it can be said that the influence of these matters upon the operation of the process of the invention is not significantly different from their influence upon related prior art multiple bed molecular sieve adsorption processes. In other words, the process of the invention is in essence seen to alter only the sequence of process steps for the use of multiple sieve beds in the separation of normal paraffins from a mixed vapor-phase hydrocarbon feed, and not to necessitate material change in the parameters recognized by the prior art as suitable for operation of any individual sieve bed. Thus, selection of such operating parameters and general procedures for the process of the invention can be made on the basis of principles well known in the art. For instance, suitable and preferred operating parameters for use in the separation of normal paraffins having from about 5 to 30 carbon atoms, and particularly those having from about 11 to 15 carbon atoms, from non-normal paraffin hydrocarbons are described in the aforementioned U.S. Pat. No. 3,451,924, the teachings of which are incorporated herein by reference.

Further illustration of the process of the invention and a comparison with prior art may be realized through the following Example and Comparative Example.

Comparative Example

According to the process of U.S. Pat. No. 3,451,924, as described above with reference to FIG. 1, three molecular sieve adsorption beds, each containing about 120,000 lbs. of a type 5A molecular sieve, are utilized to separate a vapor phase $C_{11}$ to $C_{14}$ kerosene stream of continuous and constant flowrate (882 lb moles per hour) into a normal paraffin-containing adsorbate product and a non-normal paraffin-containing raffinate product. A continuous and constant flow (1359 lb moles per hour) of normal octane eluent is supplied to the process. The temperature of all process flows and all beds is about 660° F. Feed enters the process at a pressure of approximately 42 psig; eluent is supplied at a pressure of about 65 psig. In actual practice for separation of a typical kerosene feedstock, the process of this comparative example yields an adsorbate product (average flow of about 1110 lb moles per hour) containing about 90 percent of the normal paraffins present in the feedstock and a raffinate product (average flow of approximately 1131 lb moles per hour) comprising substantially all of the feedstock's non-normal paraffin hydrocarbons.

EXAMPLE

The same three molecular sieve adsorbent beds described in the above comparative example can be used in accordance with the process of the invention for normal paraffin recovery from a continuous flow of the same kerosene feedstock. However, aspects of the invention relating to increased bed working capacity for normal paraffin adsorption permit a roughly 5 percent increase in feedstock flowrate, to 926 lb moles per hour. Process temperatures and pressures are the same as are described in the comparative example. A normal octane stream of a constant 1359 lb moles per hour would again be used as eluent.

In the steps of the process of the invention herein designated three, six, and nine, effluent from the bed in sole adsorption service is divided into a major fraction containing about 87 percent of the total and a minor fraction containing about 13 percent of the total. The major fraction is, in each case, taken as raffinate product and the minor fraction is passed through the pre-adsorption purge bed. Total flow to the pre-adsorption purge bed in each of steps three, six, and nine, is slightly in excess of that equivalent to the fill of the void space of the particular bed.

Under practice according to this example of the invention the quality of the separation of feedstock into a normal paraffin-containing adsorbate product and a non-normal paraffin-containing raffinate product would be at least equivalent to that obtained through operation of the above prior art comparative example. Process raffinate product flow is about 1029 lb moles per hour in steps 1, 4, and 7, and also in steps 2, 5, and 8. In steps 3, 6, and 9, adsorbate product totals about 929 lb moles per hour (809 lb moles per hour from the sole adsorption bed and 120 lb moles per hour from the pre-adsorption purge bed). Absorbate product flow is about 1243 lb moles per hour in steps 1, 2, 4, 5, 7, and 8, and zero lb moles per hour in steps 3, 6, and 9.

Normal paraffin concentration in the adsorbate product of this example is greater than in the product of the comparative example. Additionally, composition of the raffinate is much more nearly constant through the process steps of the invention, relative to the comparative example. The eluent contained in a bed as a result of purge guard service is not released into the raffinate all at once when the bed is first put into secondary adsorption service. Instead, this eluent is mixed slowly into the total raffinate stream. Discontinuities in composition of the raffinate and their adverse influence upon downstream processing operation are substantially diluted.

I claim as my invention:

1. A improved process for using at least three molecular sieve adsorbent beds and a continuous flow of a vapor-phase eluent to effect the resolution of a continuous flow of a vapor-phase hydrocarbon feed mixture containing normal paraffins and non-normal paraffin hydrocarbons into an adsorbate product fraction comprising normal paraffins and a raffinate product fraction comprising non-normal paraffin hydrocarbons, which process comprises repeated sequential performance of the following steps: step one, in which the feed mixture is passed through a first adsorbent bed,
effluent is withdrawn from the first bed and passed through a second adsorbent bed,
the eluent flow is passed through a third adsorbent bed,
adsorbate product is withdrawn as an effluent from the third bed, and
raffinate product is withdrawn as an effluent from the second bed;

step two, in which
the feed mixture is passed through the second bed,
the eluent flow is passed through the first bed,
effluent from the first bed is withdrawn and is passed through the third bed, and
raffinate product is withdrawn as effluent from the second bed and from the third bed;

step three, in which
the feed mixture is passed through the second bed,
the eluent flow is passed through the first bed,
adsorbate product is withdrawn as effluent from the first bed,
effluent from the second bed is withdrawn and is divided into a major fraction containing between about 50 and 95 volume percent and a minor fraction containing between about 5 and 50 volume percent,
said minor fraction is passed through the third bed, and
raffinate product is withdrawn as said major fraction of effluent from the second bed and as effluent from the third bed;

step four, in which
the feed mixture is passed through the second bed,
effluent is withdrawn from the second bed and passed through the third bed,
the eluent flow is passed through the first bed,
adsorbate product is withdrawn as effluent from the first bed, and
raffinate product is withdrawn as effluent from the third bed, step five, in which
the feed mixture is passed through the third bed,
the eluent flow is passed through the second bed,
effluent from the second bed is withdrawn and is passed through the first bed, and
raffinate product is withdrawn as effluent from the first bed and from the third bed;

step six, in which
the feed mixture is passed through the third bed,
the eluent flow is passed through the second bed,
adsorbate product is withdrawn as effluent from the second bed,
effluent from the third bed is withdrawn and is divided into a major fraction containing between about 50 and 95 volume percent and a minor fraction containing between about 5 and 50 volume percent,
said minor fraction is passed through the first bed, and
raffinate product is withdrawn as said major fraction of effluent from the third bed and as effluent from the first bed;

step seven, in which
the feed mixture is passed through the third bed,
effluent is withdrawn from the third bed and passed through the first bed,
the eluent flow is passed through the second bed,
adsorbate product is withdrawn as effluent from the second bed, and
raffinate product is withdrawn as effluent from the first bed; and step eight, in which
- the feed mixture is passed through the first bed,
- the eluent flow is passed through the third bed,
- effluent from the third bed is withdrawn and is passed through the second bed, and
- raffinate product is withdrawn as effluent from the first bed and from the second bed; and step nine, in which
- the feed mixture is passed through the first bed,
- the eluent flow is passed through the third bed,
- adsorbate product is withdrawn as effluent from the third bed,
- effluent from the first bed is withdrawn and is divided into a major fraction containing between about 50 and 95 volume percent and a minor fraction containing between about 5 and 50 volume percent,
- said minor fraction is passed through the second bed, and
- raffinate product is withdrawn as said major fraction of effluent from the first bed and as effluent from the second bed.

2. The process of claim 1, wherein the major fraction contains between about 60 and 93 volume percent and the minor fraction contains between about 7 and 40 volume percent of the effluent flow from the second bed in step three, from the third bed in step six, and from the first bed in step nine.

3. The process of claim 2, wherein the normal paraffins have between about 8 and 20 carbon atoms.

4. The process of claim 3, wherein the major fraction contains between about 70 and 90 volume percent and the minor fraction contains between about 10 and 30 volume percent of the effluent flow from the second bed in step three, from the third bed in step six, and from the first bed in step nine.

5. The process of claim 4, wherein the hydrocarbon feed mixture is kerosene.

6. The process of claim 5, wherein the normal paraffins have between about 11 and 15 carbon atoms.

7. The process of claim 6, wherein the major fraction contains between about 75 and 88 volume percent and the minor fraction contains between about 12 and 25 volume percent of the effluent flow from the second bed in step three, from the third bed in step six and from the first bed in step nine.

8. The process of claim 7, wherein the eluent flow has a mass flowrate between about four and eight times the mass flowrate of the normal paraffins in the feed mixture.

* * * * *